(12) United States Patent
von Grünberg (10) Patent No.: US 9,480,531 B2
(45) Date of Patent: Nov. 1, 2016

(54) ACTIVE DEVICE FOR POSITIONING A SURGICAL INSTRUMENT AND A SURGICAL ROBOTIC SYSTEM COMPRISING THIS DEVICE

(71) Applicant: avateramedical GmbH, Jena (DE)

(72) Inventor: Hubertus von Grünberg, Hannover (DE)

(73) Assignee: avateramedical GmbH, Jena (DE)

( * ) Notice: Subject to any disclaimer, the term of this patent is extended or adjusted under 35 U.S.C. 154(b) by 454 days.

(21) Appl. No.: 13/803,235

(22) Filed: Mar. 14, 2013

(65) Prior Publication Data
US 2014/0180308 A1    Jun. 26, 2014

(30) Foreign Application Priority Data

Dec. 20, 2012 (DE) ..................... 10 2012 025 101

(51) Int. Cl.
*A61B 19/00* (2006.01)

(52) U.S. Cl.
CPC ........... *A61B 19/2203* (2013.01); *A61B 34/30* (2016.02); *A61B 90/11* (2016.02)

(58) Field of Classification Search
CPC .... A61B 19/201; A61B 90/10; A61B 90/11; A61B 90/13; A61B 34/30; A61B 34/302; A61B 34/304; A61B 34/32; A61B 34/35; A61B 34/37; A61B 34/70; A61B 34/74; A61B 2017/3407
USPC ........................................................ 606/130
See application file for complete search history.

(56) References Cited

U.S. PATENT DOCUMENTS

| 6,558,407 B1 * | 5/2003 | Ivanko et al. ................. 606/201 |
| 6,764,445 B2 * | 7/2004 | Ramans et al. ................ 600/229 |

(Continued)

FOREIGN PATENT DOCUMENTS

| DE | 102009012987 | 2/2010 |
| EP | 2324790 | 5/2011 |

(Continued)

OTHER PUBLICATIONS

International Search Report for PCT/DE2013/000806, mailed Apr. 23, 2014.

*Primary Examiner* — Diane Yabut
*Assistant Examiner* — Martin T Ton
(74) *Attorney, Agent, or Firm* — McDonnell Boehnen Hulbert & Berghoff LLP (57) ABSTRACT

The present invention relates to an active positioning device for a surgical instrument arranged on a robot arm, comprising a carrier plate (3, 33), which can be connected with a robot arm (1, 31), a port mechanism (4, 34), which is arranged on carrier plate (3, 33) and intended as entry point into the interior of a body, at least one guide device (6, 36, 59) for insertion of a surgical instrument (8, 38, 61) into the body, whereby the shaft of surgical (8, 38, 61) instrument extends through guide device (6, 36, 59) and whereby guide device (6, 36, 59) is variably connected to port mechanism (4, 34) via a compensating element (5, 35) and an adjustment device (9, 10, 11, 12, 13, 14, 39, 40, 41, 42, 43, 44, 62, 63, 64, 65, 66, 67) for guide device (6, 36, 59) opposite port mechanism (4, 34), which is arranged on carrier plate (3, 33) and/or port mechanism (4, 34) on the one hand and guide device (6, 36, 59) on the other hand, in such a way that the shaft of surgical instrument (8, 38, 61) is movable both in x-direction and y-direction in relation to the starting position, in which the longitudinal extension of the surgical instrument runs parallel to the longitudinal extension of port mechanism (4, 34).

16 Claims, 8 Drawing Sheets

(56) References Cited

U.S. PATENT DOCUMENTS

| | | |
|---|---|---|
| 2003/0040753 A1* | 2/2003 | Daum et al. .................... 606/96 |
| 2010/0042111 A1* | 2/2010 | Qureshi et al. ............... 606/130 |
| 2010/0234856 A1 | 9/2010 | Stoianovici et al. |
| 2011/0152717 A1 | 6/2011 | Kim et al. |
| 2011/0319913 A1* | 12/2011 | Labadie et al. ............... 606/130 |
| 2012/0116362 A1* | 5/2012 | Kieturakis ....................... 606/1 |
| 2013/0317521 A1 | 11/2013 | Choi et al. |

FOREIGN PATENT DOCUMENTS

| | | |
|---|---|---|
| WO | 2006/035143 | 4/2006 |
| WO | 2009057117 | 5/2009 |

* cited by examiner

ACTIVE DEVICE FOR POSITIONING A SURGICAL INSTRUMENT AND A SURGICAL ROBOTIC SYSTEM COMPRISING THIS DEVICE

CROSS-REFERENCE

This application claims priority to German patent application serial no. DE 10-2012 025 101.7 filed Dec. 20, 2012, incorporated by reference herein in its entirety.

FIELD OF THE INVENTION

The present invention relates to an active positioning device for a surgical instrument and a surgical robot system or telemanipulator for minimally invasive surgery and particularly laparoscopy.

BACKGROUND

Robot systems or telemanipulators for minimally invasive surgery, particularly for laparoscopic surgery, replace the surgical instruments usually operated manually by the surgeon, e.g. surgical instruments, endoscopes, or camera, with a motorized positioning mechanism. The surgical instruments to be used are guided inside a patient's body via one or several trocars. A trocar refers to an instrument used by the surgeon in minimally invasive surgery to gain access to the patient's body cavity (usually the abdomen or thorax), whereby the port is kept open by a tube, a so-called tubus. The robot system provides a moving mechanism and control logic, which allows for the movement of the surgical instruments about a pivot point in 2 degrees of freedom (x, y) and a translational movement of the surgical instruments along the axis of the instrument (z). The pivot point refers to the invariant point of the motion in 2 degrees of freedom (x, y). This pivot point is ideally located at the point where the trocar penetrates the patient's abdominal wall. The control logic of a robot system must know the pivot point or the pivot point must be defined by the moving mechanism's design, to limit the surgical instrument's movement in a way that keeps the biomechanical stress acting on the tissue around the trocar at a minimum.

Robot systems known from prior art are based on robot arms for passive prepositioning and active moving of a surgical instrument. A solution based on prior art robot arms, which implement passive prepositioning and active moving of surgical instruments about a pivot point, requires a large installation space on the one hand and the motion sequences of the robot arms can lead to a collision on the other hand.

During a minimally invasive surgical procedure a minimum of two, usually three to four surgical instruments, such as gripper, scissors, needle holder, dissector, as well as a camera or an endoscope are used, which are each inserted into the patient's body via a separate trocar. This means that there is a robot arm for each employed surgical instrument, controlling the passive prepositioning and active moving of the instrument.

The disadvantage of the prior art solutions lies in the fact that the position of the patient has to be fixed before surgery commences and that repositioning the patient during surgery is near impossible. Another disadvantage already mentioned is the large installation space existing robot systems require.

SUMMARY OF THE INVENTION

In one aspect, the present invention provides an active positioning devices for a surgical instrument for use on a robot arm, comprising:

a carrier plate connected to a robot arm,
a port mechanism that is arranged on the carrier plate and intended as an entry point into an interior of a body,
at least one guide device for inserting a surgical instrument into the body, whereby a shaft of the surgical instrument extends through a guide device and whereby the guide device is variably connected to the port mechanism via a compensating element, and
an adjustment device for the guide device opposite to the port mechanism, wherein the adjustment device is arranged on one of the carrier plate, the port mechanism, or the guide device in such a way that the shaft of the surgical instrument is movable in two directions orthogonal to each other, an x-direction and a y-direction in relation to a starting position, in which a longitudinal extension of the surgical instrument runs parallel to a longitudinal extension of the port mechanism.

In one embodiment, the geometry of the compensating element is variable in such a way that a freely selectable angle can be set for both the x-direction and the y-direction between the port mechanism and the guide device with regard to the starting position, in which they are congruent to each other, whereby the compensating element is particularly made from elastic material. In another embodiment, the adjustment device comprises at least two controllable actuators, which in particular are designed as actuating drives that are arranged orthogonally to each other, whereby a ball lever mechanism is provided in-between the guide device and the carrier plate or the port mechanism in such a way that per the actuating drives, by means of the ball lever mechanism, the guide device can be independently positioned in the x-direction and the y-direction in relation to the starting position. In a further embodiment, a translation adjustment device is provided on the guide device, said translation adjustment device being connected to the surgical instrument in such a way that the shaft of the surgical instrument is movable in a z-direction which is orthogonal to the x-direction and y-direction. In another embodiment, the translation adjustment device moves the shaft of the surgical instrument in the z-direction by means of a telescopic mechanism and/or a cable winch system. In a further embodiment, an instrument drive unit is provided on the surgical instrument, said instrument drive unit comprising a rotational actuator, by means of which the shaft of the surgical instrument is variably rotated around the z-direction in relation to the starting position. In a still further embodiment, the instrument drive unit preferably comprises three instrument actuators by means of which a work unit of the surgical instrument, arranged on the distal end, is variable in three further degrees of freedom. In a further embodiment, the instrument drive unit is arranged on the proximal end of the telescopic mechanism by means of a holding device. In another embodiment, two guide devices are intended for insertion of two surgical instruments through a compensating element, whereby an adjustment device of a first of the two guide devices is arranged in a mirror-inverted manner with regard to a longitudinal axis of the two guide devices to the active positioning device of a second of the two guide devices.

In another aspect, the present invention provides a surgical robot systems, comprising:
a control system, which can be operated by a user to perform a surgical procedure,
a support structure, on which two or more robot arms are arranged, which are movable by means of the control system and whereby an active positioning device of a surgical instrument is provided on at least one robot arm, wherein the robotic arm comprises:

a carrier plate, which can be connected with a robot arm, a port mechanism that is arranged on the carrier plate and intended as an entry point into the interior of a body, at least one guide device for inserting a surgical instrument into the body, whereby a shaft of the surgical instrument extends through a guide device and whereby the guide device is variably connected to the port mechanism via a compensating element, and an adjustment device for the guide device opposite to the port mechanism, wherein the adjustment device is arranged on one of the carrier plate, the port mechanism, or the guide device in such a way that the shaft of the surgical instrument is movable in two directions orthogonal to each other, an x-direction and a y-direction in relation to a starting position, in which a longitudinal extension of the surgical instrument runs parallel to a longitudinal extension of the port mechanism.

In one embodiment, the geometry of the compensating element is variable in such a way that a freely selectable angle can be set for both the x-direction and the y-direction between the port mechanism and the guide device with regard to the starting position, in which they are congruent to each other, whereby the compensating element is particularly made from elastic material. In another embodiment, the adjustment device comprises at least two controllable actuators, which in particular are designed as actuating drives that are arranged orthogonally to each other, whereby a ball lever mechanism is provided in-between the guide device and the carrier plate or the port mechanism in such a way that per the actuating drives, by means of the ball lever mechanism, the guide device can be independently positioned in the x-direction and the y-direction in relation to the starting position. In a further embodiment, a translation adjustment device is provided on the guide device, said translation adjustment device being connected to the surgical instrument in such a way that the shaft of the surgical instrument is movable in a z-direction which is orthogonal to the x-direction and y-direction. In another embodiment, the translation adjustment device moves the shaft of the surgical instrument in the z-direction by means of a telescopic mechanism and/or a cable winch system. In a still further embodiment, an instrument drive unit is provided on the surgical instrument, said instrument drive unit comprising a rotational actuator, by means of which the shaft of the surgical instrument is variably rotated around the z-direction in relation to the starting position. In another embodiment, the instrument drive unit preferably comprises three instrument actuators by means of which a work unit of the surgical instrument, arranged on the distal end, is variable in three further degrees of freedom. In a further embodiment, the instrument drive unit is arranged on the proximal end of the telescopic mechanism by means of a holding device. In yet another embodiment, two guide devices are intended for insertion of two surgical instruments through a compensating element, whereby an adjustment device of a first of the two guide devices is arranged in a mirror-inverted manner with regard to a longitudinal axis of the two guide devices to the active positioning device of a second of the two guide devices.

DESCRIPTION OF THE FIGURES

The present invention is implemented in purely exemplary manner by the attached figures.

DETAILED DESCRIPTION OF THE INVENTION

It is therefore the object of the present invention to provide an active positioning device for a surgical instrument and a surgical robot system, which provides high variability and requires only limited installation space or is of a smaller and lighter embodiment.

It is another object of the present invention to provide a robot system that allows for the repositioning of a patient during surgery, in particular without limiting the freedom of movement of the surgical instrument after repositioning.

These objects are achieved, according to the present invention, by active positioning devices and surgical robot systems as disclosed herein.

One subject-matter of the present invention concerns an active positioning device of a surgical instrument for use on a robot arm comprising:

a carrier plate connected to a robot arm, a port mechanism that is arranged on the carrier plate and intended as an entry point into an interior of a body, at least one guide device for inserting a surgical instrument into the body, whereby a shaft of the surgical instrument extends through a guide device and whereby the guide device is variably connected to the port mechanism via a compensating element, and an adjustment device for the guide device opposite to the port mechanism, wherein the adjustment device is arranged on one of the carrier plate, the port mechanism, or the guide device in such a way that the shaft of the surgical instrument is movable in two directions orthogonal to each other, an x-direction and a y-direction in relation to a starting position, in which a longitudinal extension of the surgical instrument runs parallel to a longitudinal extension of the port mechanism.

In a preferred embodiment the geometry of the compensating element is variable in such a way that a freely selectable angle can be set for both the x-direction and the y-direction between the port mechanism and the guide device with regard to the starting position, in which they are congruent to each other, whereby the compensating element is particularly made from elastic material.

In another preferred embodiment the adjustment device comprises at least two controllable actuators, which in particular are designed as actuating drives that are arranged orthogonally to each other, whereby a ball lever mechanism his provided in-between the guide device and the carrier plate or the port mechanism in such a way that per the actuating drives, by means of the ball lever mechanism, the guide device can be independently positioned in the x-direction and the y-direction in relation to the starting position.

In yet another preferred embodiment a translation adjustment device is provided on the guide device, said translation adjustment device being connected to the surgical instrument in such a way that the shaft of the surgical instrument is movable in a z-direction which is orthogonal to the x-direction and y-direction. Preferably the translation adjustment device moves the shaft of the surgical instrument in the z-direction by means of a telescopic mechanism and/or a cable winch system.

In a further preferred embodiment an instrument drive unit is provided on the surgical instrument, said instrument drive unit comprising a rotational actuator, by means of which the shaft of the surgical instrument is variably rotated around the z-direction in relation to the starting position. The instrument drive unit preferably comprises three instrument actuators by means of which a work unit of the surgical instrument, arranged on the distal end, is variable in three further degrees of freedom. It is particularly preferred that the instrument drive unit is arranged on the proximal end of the telescopic mechanism by means of a holding device.

A further subject-matter of the present invention concerns a surgical robot system for performing surgical procedures on the human body, comprising:

a control system, which can be operated by a user to perform a surgical procedure, a support structure, on which two or more robot arms are arranged, which are movable by means of the control system and whereby an active positioning device of a surgical instrument is provided on at least one robot arm, wherein the robotic arm comprises:

a carrier plate, which can be connected with a robot arm, a port mechanism that is arranged on the carrier plate and intended as an entry point into the interior of a body, at least one guide device for inserting a surgical instrument into the body, whereby a shaft of the surgical instrument extends through a guide device and whereby the guide device is variably connected to the port mechanism via a compensating element, and an adjustment device for the guide device opposite to the port mechanism, wherein the adjustment device is arranged on one of the carrier plate, the port mechanism, or the guide device in such a way that the shaft of the surgical instrument is movable in two directions orthogonal to each other, an x-direction and a y-direction in relation to a starting position, in which a longitudinal extension of the surgical instrument runs parallel to a longitudinal extension of the port mechanism.

In a preferred embodiment of the robot system the geometry of the compensating element is variable in such a way that a freely selectable angle can be set for both the x-direction and the y-direction between the port mechanism and the guide device with regard to the starting position, in which they are congruent to each other, whereby the compensating element is particularly made from elastic material.

Further advantageous embodiments of the surgical robot system, according to the invention, arise from the subclaims analogous to the active positioning device for a surgical instrument. This is achieved in particular by the fact that the active positioning device, according to the invention, can be combined or upgraded with a robot system. The surgical robot system can be used, for example, for performing surgical procedures on the human body.

According to the invention, the terms robot system and telemanipulator can be used synonymously.

Figure 6:
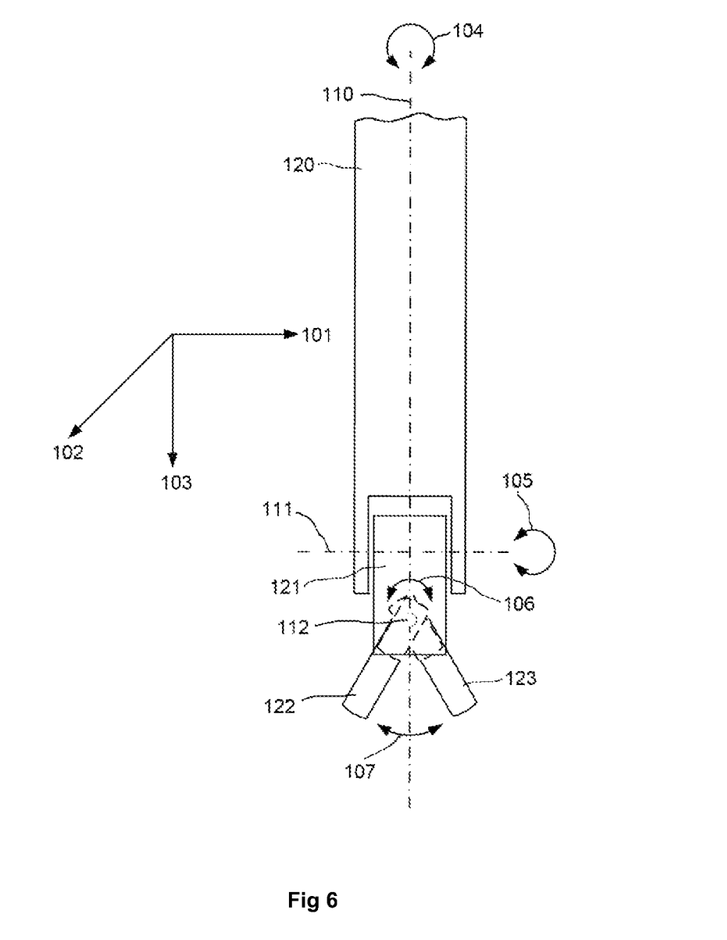
FIG. 6 shows a schematic view of a surgical instrument, which can be part of the invention.

In one aspect, the present invention relates to a surgical robot system or telemanipulator that combines a passive prepositioning of the trocar or of the active positioning device with an active control or motorization of the trocar for the purpose of moving a surgical instrument. Such an "active trocar" according to the invention can move the surgical instrument about the pivot point in at least 2 degrees of freedom (direction 101 and 102), as shown in FIG. 6. According to the invention, the surgical instruments have 7 degrees of freedom: 3 degrees of freedom (degrees of freedom 101, 102, and 103 in accordance with FIG. 6) are implemented by means of a motorized coupling of the surgical instrument inserted in the trocar with corresponding drive units, additional 4 degrees of freedom (degrees of freedom 104, 105, 106, and 107 in accordance with FIG. 6) are implemented by means of a drive unit on the end of each employed surgical instrument.

Due to the fact that the pivot point is defined by the active trocar itself, the position of the pivot point is determined before the start of the surgery by means of a prepositioning of the active trocar. This makes repositioning the patient after the start of the surgical procedure possible, since the pivot point is physically connected with the positioning devices or active trocars according to the invention and is maintained in relation to the active positioning device during repositioning, i.e. the pivot point is maintained in relation to the instrument and the carrier plate and the guide device, at all times.

Furthermore, the system can be implemented significantly smaller and lighter, because no robot arms for active positioning are used. This allows for a simpler transfer of the entire system, for example to a different operating room, and therefore for higher flexibility and utilization.

Figure 1:
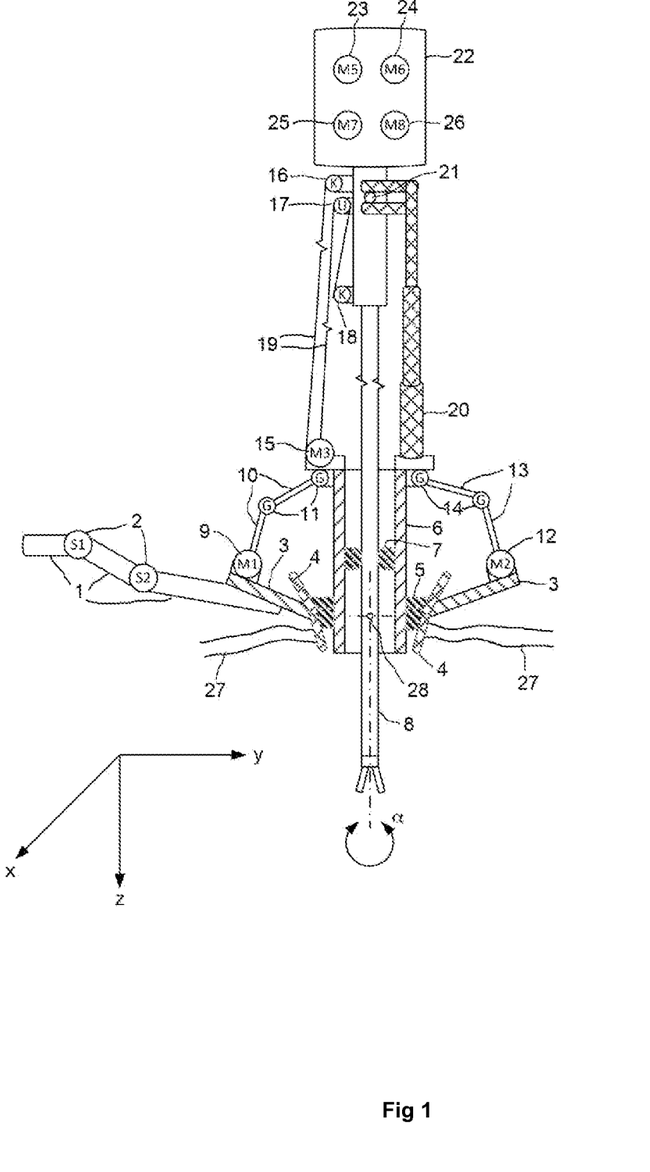
FIG. 1 shows a schematic view of the active positioning device of a surgical instrument according to the invention arranged on a robot arm.

In the following, the present invention is described in detail with reference to the Figures:

FIG. 1 shows an active positioning device of a surgical instrument according to the invention arranged on a robot arm. Generally, 4 surgical instruments are used during a minimally invasive laparoscopic procedure, 3 of which are surgical instruments and 1 camera or endoscope, which are controlled by the surgeon by means of the telemanipulator system. According to the invention, the system comprises preferably 4 embodiments of an active trocar or active positioning device. However, it is recognized that embodiments with 1 to 3 or more than 4 active trocars are also within the scope of protection of the invention. Every active trocar is mounted via a robot arm 1, which can be furnished with joints 2, in weight force-free fashion. This mounting mechanism must be provided for each active trocar, accordingly. All mounting mechanisms can be mounted on a mutual carrier (see FIG. 4) or on separate carriers. Mounting on separate carriers can be useful, for example, if the arrangement of the trocars for the surgical procedure requires it.

A carrier plate 3 of the active trocar is rigidly connected with robot arm 1. Carrier plate 3, in turn, is rigidly connected with a port mechanism 4. Port mechanism 4 is connected with guide device 6 via a compensating element 5. A movement (inclination) of guide device 6 in relation to port mechanism 4 is possible by means of compensating element 5. Through this movement the pivotal movement of surgical instrument 8 about pivot point 28 is implemented. Surgical instrument 9 enters into guide device 6. A gas-tight sealing of surgical instrument 8 against guide device 6 is achieved by means of a sealing ring 7. During the laparoscopy the abdominal cavity is "inflated" through introduction of a gas (carbon dioxide, $CO_2$), to provide the surgeon with more freedom of movement during the actual surgical procedure. Sealing 7 is necessary to prevent the gas from escaping.

Actuators or actuating drives 9, 12 are arranged orthogonally to each other. Forces act upon the top end of guide device 6 via a ball lever mechanism 10, 11 and 13, 14, so that said guide device is movable on 2 axes (x, y), relative to port mechanism 4, independently of each other.

A further actuating drive 15 is arranged on the top end of guide device 6. The instrument's translational movement in z-direction is achieved by means of an actuating drive mechanism comprising clamp 16, deflection roller 17, clamp 18 and corresponding cable winches 19.

A telescopic mechanism 20 is connected with an instrument drive unit 22 via holding device 21 in such a way that a rotational movement α of surgical instrument 8 about z-axis is prevented. The rotational movement α of surgical instrument 8 is achieved by means of a rotational actuator 23 connected to the shaft of surgical instrument 8. Instrument actuators 24, 25 and 26 implement the movements of surgical instrument 8 in degrees of freedom 105, 106 and 107, see FIG. 6.

Figure 2:
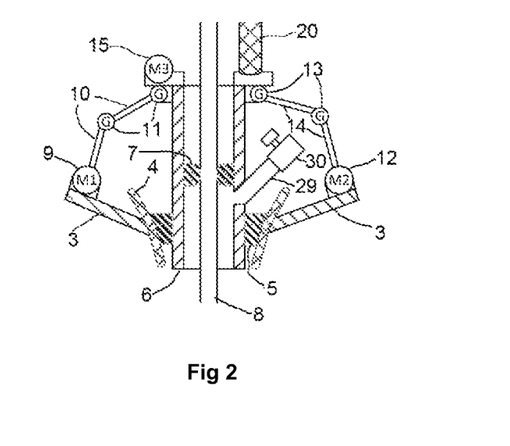
FIG. 2 shows a partial schematic view of the active positioning device according to the invention with a connection option for administering insufflation gas, usually $CO_2$.

FIG. 2 shows an active positioning device according to the invention in accordance with FIG. 1, additionally equipped with an insufflation connector comprising a feeding tube (29) leading into the hollow space of trocar (6) below sealing (7) and a connection and valve assembly (30). An insufflation device is connected to the connection and valve assembly. Said insufflation device pumps a gas, usually $CO_2$, into the patient's abdominal cavity via valve assembly (30) and feeding tube (29) connected thereto. Sealing (7) prevents unintended escaping of gas from the patient's abdominal cavity into the environment. Sealing (7) is expediently designed in such a way that it seals trocar (6) in gas-tight manner during complete removal of instrument (8) from said trocar, i.e. no insufflation gas escapes into the environment, even after the instrument has been removed.

Figure 3:
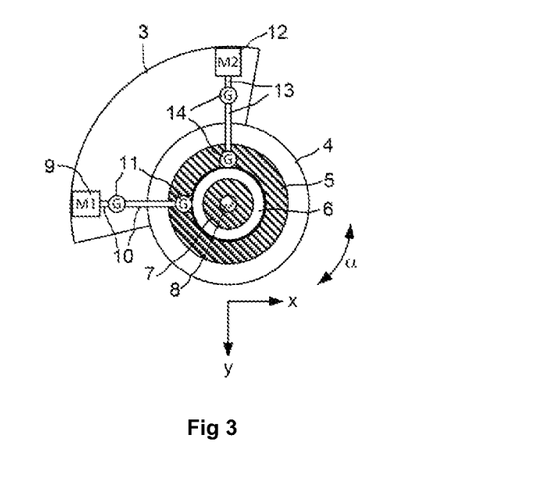
FIG. 3 shows a top view of the active positioning device in accordance with FIG. 1.

FIG. 3 shows a top view of the active positioning device in accordance with FIG. 1.

Figure 4:
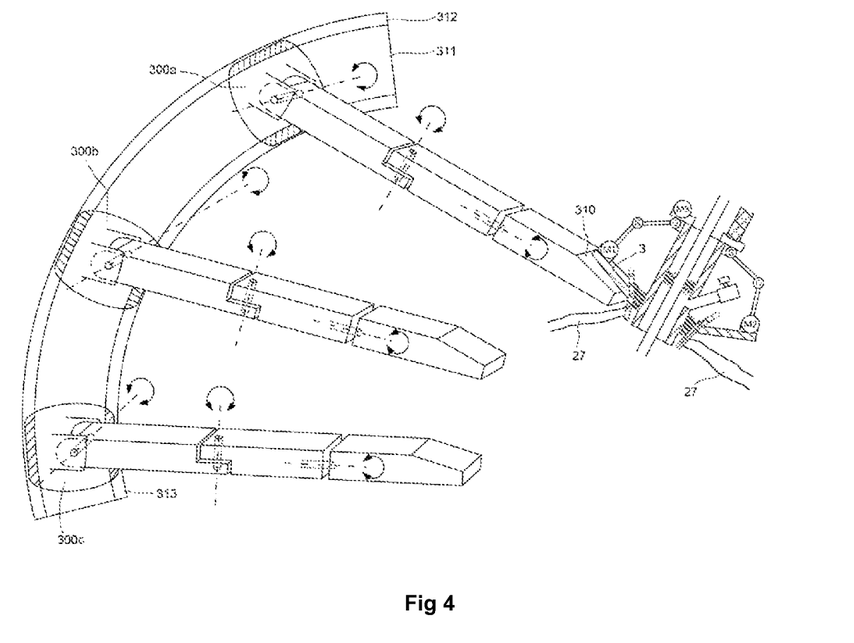
FIG. 4 shows a schematic view of a part of the surgical robot system according to the invention during surgery on a human body.
Figure 5:
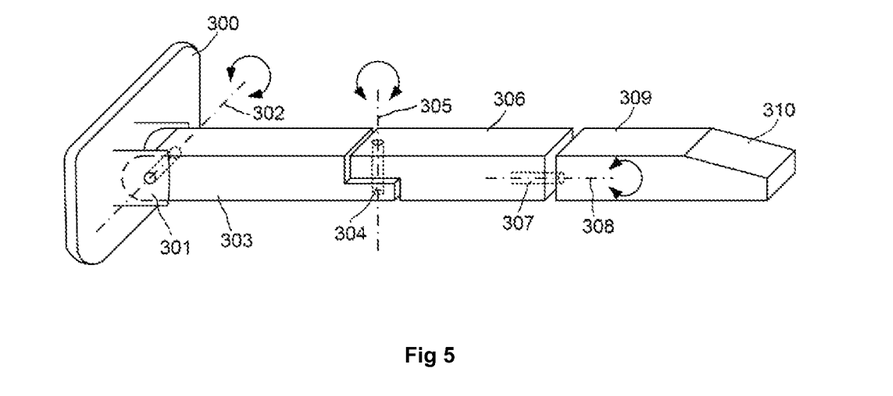
FIG. 5 shows a schematic view of a robotic arm according to the invention.

FIG. 4 shows a schematic view of a part of the surgical robot system according to the invention during surgery on a human body; the robot arms, as described in detail in FIG. 5, are mounted via mounting bases, in this example 300a, 300b and 300c, in such a way that these mounting bases are mounted in an e.g. arched-shaped guide rail 311 in connection with 312 and 313 and can be positioned independently in relation to each other. The active positioning device in accordance with FIG. 1 or 2 is mounted on assembly 3 at coupling surface 310 of the robot arm. The preferably arch-shaped form of the guide is advantageous in that the robot arms can be prepositioned in accordance with the typical anatomy of a patient in an arch above abdominal wall 27.

FIG. 5 shows a schematic view of a robotic arm according to the invention; the robot arm comprises multiple links 303, 306 and 309 connected to each other via joints in such a way that an arrangement of coupling surface 310 with an active positioning device in accordance with FIG. 1 or 2 is possible. The robot arm itself is mounted on a mounting base 300 via a joint 301 that allows for a pivoting motion about axis of rotation 302 of +/−90°. First partial link 303 of the robot arm leads to a further joint 304 comprising an axis of rotation 305, preferably orthogonally in relation to axis of rotation 302. A further partial link 306 of the robot arm is connected via joint 304, said partial link enabling a pivoting motion 308 via a further joint 307, preferably arranged orthogonally in relation to axis of rotation 302 and orthogonally in relation to axis of rotation 305. The third partial link 309 of the robot arm comprises a coupling surface 310 on its distal end, on which coupling surface the active positioning device can be mounted on assembly 3, by creating a suitable force-locking and preferably also form-locking connection, in accordance with FIG. 1 or 2. Joints 301, 304, 307 can be implemented actively, i.e. comprising actuating drives, or passively. Joints 301, 304, 307 are equipped with absolute position monitoring systems so that the position or orientation in space of the robot arms and the respectively active positioning device attached to them is known. The signals of the absolute position monitoring systems can preferably be connected in control unit 202 in such a way that, knowing the geometry and current position of the active positioning device in accordance with FIG. 1 or 2, an impeding collision of the different robot arms with each other or the collision of a robot arm with an active positioning device of another robot arm is recognized and a collision warning can be given to the user via operating and display unit 200. In another embodiment control unit 202 can actively prevent the potential collision of the different robot arms with each other or the collision of a robot arm with an active positioning device of another robot arm, by changing the positioning command given by operating and display unit 200. In a passive embodiment, joints 301, 304, 307 are preferably safeguarded by a device against unintentional adjustment of the joint position.

FIG. 6 shows a surgical instrument as a possible part of the invention. Overall, the design has 7 Degrees of Freedom. These are implemented by a translational movement of instrument shaft (120) in x-direction (101) and y-direction (102). These movements bring about a tilting of the instrument about the pivot point. Furthermore, instrument shaft (120) can be moved in z-direction (103). The instrument shaft (120) can be rotated around its own instrument axis (110) in direction of movement (104). The tip of the instrument comprises at least 3 assemblies that are movable relative to each other. A first assembly (121) is movably arranged around the axis of rotation (111) in direction of rotation (105), tiltable towards instrument shaft (120). Assembly (121) itself comprises two assemblies (122, 123), being tiltably arranged, independently of each other, around the axis of rotation (112) in direction of rotation (106). The rotational movement of assembly (122) in relation to assembly (123) alters angle (107) between the two assemblies (122, 123) around axis of rotation (112). This allows for executing a gripping, clamping, or cutting motion, depending on how assemblies (122, 123) are mechanically formed.

Figure 7:
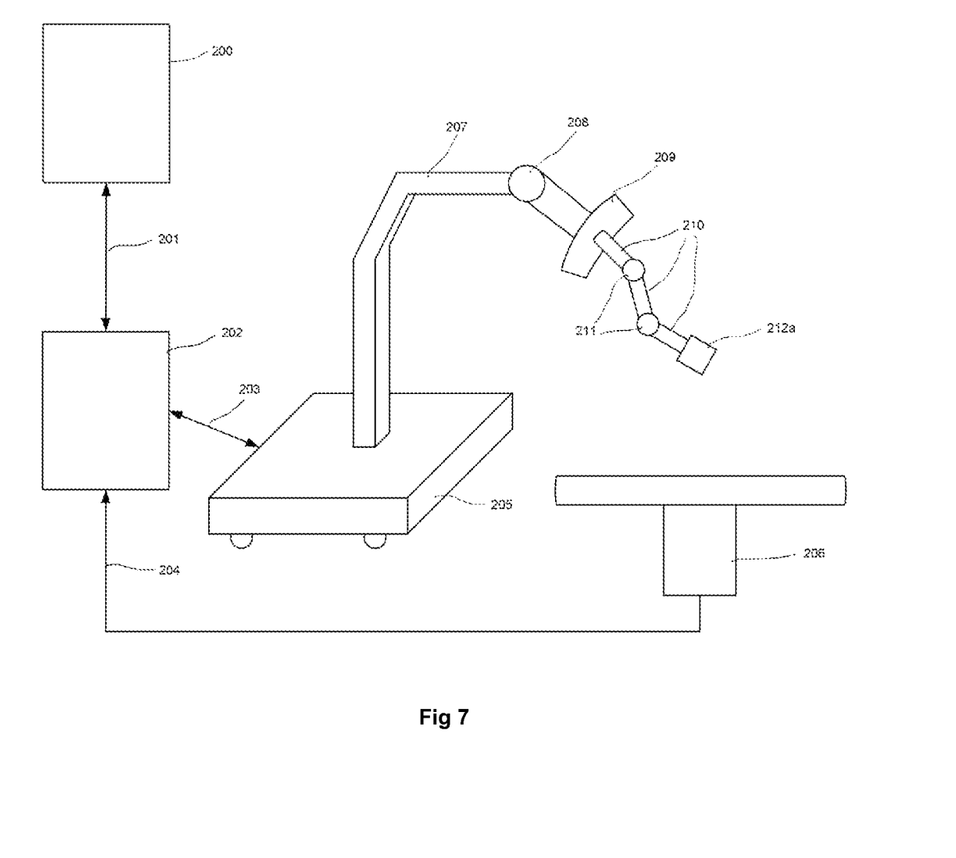
FIG. 7 shows a schematic view of a robot system with a robot arm and active positioning devices according to the invention.
Figure 8:
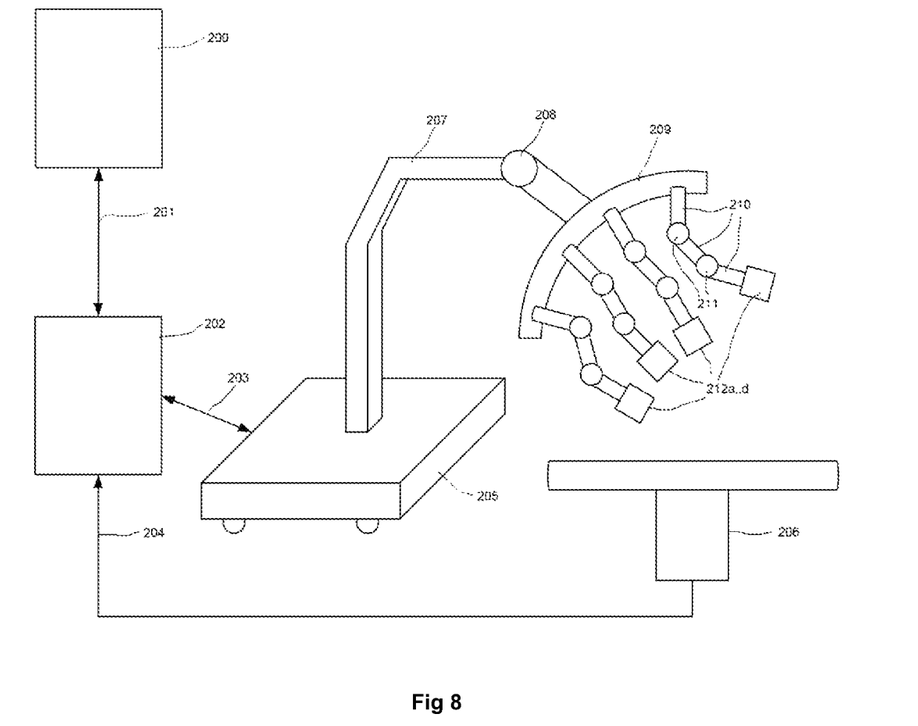
FIG. 8 shows a schematic view of a robotic system with 4 robot arms and active positioning devices according to the invention.

FIG. 7 and FIG. 8 show embodiments of the robot system according to the invention with one or 4 robot arms and one (212a) or 4 (212a-d) active positioning devices according to the invention. The following descriptions concern an embodiment with a robot arm in accordance with FIG. 7. The active positioning device (212a) is connected with an arc-shaped guide (209) via a prepositioning device consisting of assemblies 210 and 211. The implementation of the prepositioning device can be passive, i.e. by means of manual adjustment or preferably also active, i.e. by means of equipping the joints (211) with active actuating drives. The prepositioning device itself is mounted with a suitable mount, e.g. as arc-shaped guide (209). This arc-shaped guide (209) can be positioned towards the patient by means of joint (208). Cantilever (207) is connected with mobile carrier system (205), making the positioning of the entire carrier system (comprising 205, 207 . . . 212a) in relation to operating table (206) possible. The user is informed of the current status of prepositioning device (210, 211) via the operating and display unit. The user can enter control commands via operating and display unit (200), said control commands being sent via a suitable data connection (201) to control unit (202) and from said control unit to active positioning device (212a), prepositioning device (210, 211) and arc-shaped guide (209) for further processing. Control unit (202) is connected to a suitable data connection (203) via a carrier system. In case of a change to the position of the operating table, e.g. to its height, it is also possible for the technical control of operating table (206) to be linked to control unit (202) via data connection (204), to achieve active tracking of active positioning device (212a) via prepositioning device (210, 211) and/or the position of arc-shaped guide (209). This allows for active compensation for changes to the position of the patient resulting from changes to the position of operating table (206).

Figure 9:
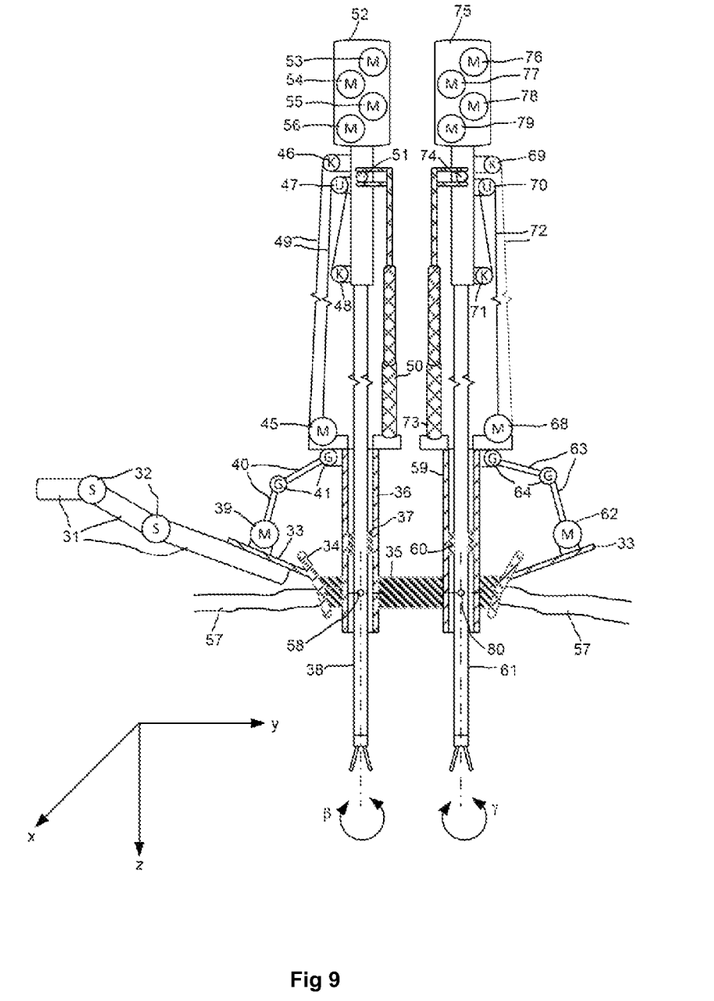
FIG. 9 shows a schematic view of the active positioning device according to the invention for two surgical instruments and a mutual port, arranged on a robot arm.
Figure 10:
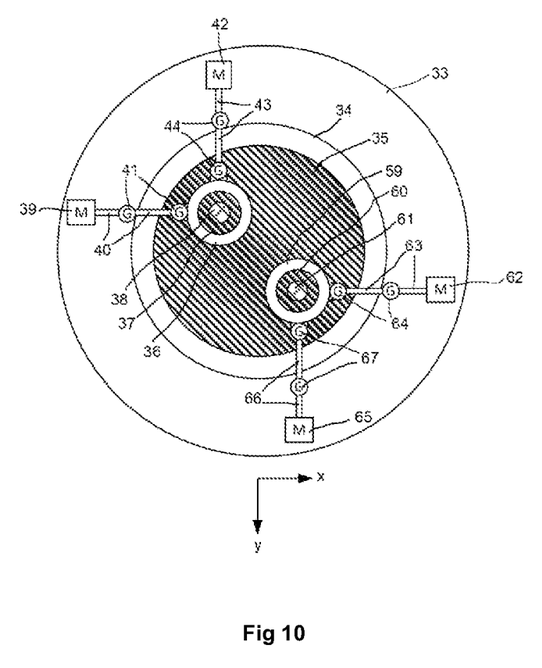
FIG. 10 shows a top view of the active positioning device in accordance with FIG. 9.

FIG. 9 and FIG. 10 show an active positioning device according to the invention for two surgical instruments on a mutual port, arranged on a robot arm. Generally, 4 surgical instruments are used during a minimally invasive laparoscopic procedure, 3 of which are surgical instruments and 1 camera or endoscope, which are controlled by the surgeon by means of the telemanipulator system. Therefore, according to the invention, 2 surgical instruments can be inserted into the patient's body via a mutual port (single-port) by means of two separate guide device and controlled independently from each other by means of respectively one active positioning device per each surgical instrument. According to this, the system comprises preferably 2 embodiments of an active trocar for a single port access or of an active positioning device. It is recognized, however, that embodiments with 1 or more than 2 active trocars for a single port access are also within the scope of protection of the invention Every active trocar is mounted via a robot arm 31, which can be furnished with joints 32, in weight force-free fashion. This mounting mechanism must be provided for each active trocar, accordingly. All mounting mechanisms can be arranged on a mutual carrier (see FIG. 4) or on separate carriers. Mounting on separate carriers can be useful, for example, if the arrangement of the trocars for the surgical procedure requires it.

A carrier plate 33 of the active trocar is rigidly connected with robot arm 31. Carrier plate 33, in turn, is rigidly connected with a port mechanism 34. Port mechanism 34 is connected with guide devices 36 and 59 via compensating element 35. Compensating element 35 makes a movement (tilt) of guide devices 36 and 50 in relation to port mechanism 34 possible. Through this movement the pivotal movement of surgical instruments 38 and 61 is implemented. Guide devices 36 and 59 receive surgical instruments 38 and 61. A gas-tight sealing of surgical instruments 38 and 61 against guide devices 36 and 59 is achieved through sealing rings 37 and 60. During the laparoscopy the abdominal cavity is "inflated" through introduction of a gas (carbon dioxide, $CO_2$), to provide the surgeon with more freedom of movement during the actual surgical procedure. Sealing 37 or 60 is necessary to prevent gas from escaping.

Actuators or actuating drives 39, 42 and 62, 65 are arranged orthogonally to each other. Forces act upon the top end of guide devices 36 or 59 by means of ball lever mechanisms 40, 41, 43, 44 and 63, 64, 66, 67, so that said guide devices can be moved independently from each other in relation to port mechanism 34 on 2 axes (x, y).

Further actuating drives 45, 68 are arranged on the top ends of guide devices 36 and 59. The translational movement of instrument 38 in z-direction is achieved by means of actuating drive mechanisms comprising clamp 46, deflection roller 47, clamp 48 and corresponding cable winches 49. The translational movement of instrument 61 in z-direction is achieved by means of actuating drive mechanisms comprising clamp 69, deflection roller 70, clamp 71 and corresponding cable winches 72.

A telescopic mechanism 50 is connected with an instrument drive unit 52 via holding device 51 in such a way that a rotational movement β of surgical instrument 38 about the z-axis is prevented. The rotational movement β of surgical instrument 38 is achieved by means of a rotational actuator 53 connected to the shaft of surgical instrument 38. Instrument actuators 54, 55 and 56 implement the movements of surgical instrument 38 in degrees of freedom 105, 106 and 107, see FIG. 6.

A telescopic mechanism 73 is connected with an instrument drive unit 75 via holding device 74 in such a way that a rotational movement γ of surgical instrument 61 about the z-axis is prevented. The rotational movement γ of surgical instrument 61 is achieved by means of a rotational actuator 76 connected to the shaft of surgical instrument 61. Instrument actuators 77, 78 and 79 implement the movements of surgical instrument 61 in degrees of freedom 105, 106 and 107, see FIG. 6.

FIG. 10 shows a top view of the active positioning device in accordance with FIG. 9, from which can be seen that two guide devices 36, 59 pass through mutual compensating element 35. It can be especially seen from FIG. 10 that first adjustment device 39, 40, 41, 42, 43, 44 for first guide device 36 and second adjustment device 62, 63, 64, 65, 66, 67 of second guide device 59 for the two surgical instruments are arranged in such a way that an obstruction or limitation of each of the two adjustment devices is prevented.

Therefore, the present invention in total concerns an active positioning device that comprises one or several surgical instruments that can be used for minimally invasive surgery through a trocar.

The invention claimed is:

1. An active positioning device for a surgical instrument for use on a robot arm comprising:
   a carrier plate connected to a robot arm,
   a port mechanism that is arranged on the carrier plate and intended as an entry point into an interior of a body,
   at least one guide device for inserting a surgical instrument into the body, whereby a shaft of the surgical instrument extends through a guide device of the at least one guide device, and whereby the guide device is variably connected to the port mechanism via a compensating element, and
   an adjustment device for the guide device opposite to the port mechanism, wherein the adjustment device is arranged on one of the carrier plate, the port mechanism, or the guide device in such a way that the shaft of the surgical instrument is movable about a pivot point in two directions orthogonal to each other, an x-direction and a y-direction in relation to the port mechanism, in which a longitudinal extension of the surgical instrument runs parallel to a longitudinal extension of the port mechanism, wherein the adjustment device comprises exactly two controllable actuators which are designed as actuating drives that are arranged orthogonally to each other, whereby a ball lever mechanism is provided in-between the guide device and the carrier plate or the port mechanism in such a way that, per the actuating the drives, by means of the ball lever mechanism, the guide device is independently positioned in the x-direction by a first one of the two actuators and the y-direction by a second one of the two actuators in relation to the port mechanism.

2. The active positioning device as defined in claim 1, characterized in that the geometry of the compensating element is variable in such a way that a freely selectable angle can be set for both the x-direction and the y-direction between the port mechanism and the guide device with regard to the port mechanism, in which they are congruent to each other, whereby the compensating element is made from elastic material.

3. The active positioning device as defined in claim 1, characterized in that a translation adjustment device is provided on the guide device, said translation adjustment device comprising a further actuating drive and being connected to the surgical instrument in such a way that the shaft of the surgical instrument is movable by the further actuating drive in a z-direction which is orthogonal to the x-direction and y-direction.

4. The active positioning device as defined in claim 3, characterized in that the translation adjustment device moves the shaft of the surgical instrument in the z-direction by means of a telescopic mechanism and/or a cable winch system.

5. The active positioning device as defined in claim 1, characterized in that an instrument drive unit is provided on the surgical instrument, said instrument drive unit comprising a rotational actuator, by means of which the shaft of the surgical instrument is variably rotated around the z-direction in relation to the port mechanism.

6. The active positioning device as defined in claim 5, characterized in that the instrument drive unit preferably comprises three instrument actuators by means of which a work unit of the surgical instrument, arranged on the distal end, is variable in three further degrees of freedom.

7. The active positioning device as defined in claim 5 characterized in that the instrument drive unit is arranged on the proximal end of a telescopic mechanism by means of a holding device.

8. The active positioning device as defined in claim 1, characterized in that two guide devices are intended for insertion of two surgical instruments through the compensating element, whereby an adjustment device of a first of the two guide devices is arranged in a mirror-inverted manner with regard to a longitudinal axis of the two guide devices to an adjustment device of a second of the two guide devices.

9. A surgical robot system, comprising:
a control system, which can be operated by a user to perform a surgical procedure,
a support structure, on which two or more robot arms are arranged, which are movable by means of the control system,
and whereby an active positioning device of a surgical instrument is provided on at least one robot arm, wherein the robotic arm comprises:
a carrier plate, which can be connected with a robot arm,
a port mechanism that is arranged on the carrier plate and intended as an entry point into the interior of a body,
at least one guide device for inserting a surgical instrument into the body, whereby a shaft of the surgical instrument extends through a guide device of the at least one guide device, and whereby the guide device is variably connected to the port mechanism via a compensating element, and
an adjustment device for the guide device opposite to the port mechanism, wherein the adjustment device is arranged on one of the carrier plate, the port mechanism, or the guide device in such a way that the shaft of the surgical instrument is movable about a pivot point in two directions orthogonal to each other, an x-direction and a y-direction in relation to the port mechanism, in which a longitudinal extension of the surgical instrument runs parallel to a longitudinal extension of the port mechanism, wherein the adjustment device comprises exactly two controllable actuators which are designed as actuating drives that are arranged orthogonally to each other, whereby a ball lever mechanism is provided in-between the guide device and the carrier plate or the port mechanism in such a way that, per the actuating the drives, by means of the ball lever mechanism, the guide device is independently positioned in the x-direction by a first one of the two actuators and the y-direction by a second one of the two actuators in relation to the port mechanism.

10. The surgical robot system as defined in claim 9, characterized in that the geometry of the compensating element is variable in such a way that a freely selectable angle can be set for both the x-direction and the y-direction between the port mechanism and the guide device with regard to the port mechanism, in which they are congruent to each other, whereby the compensating element is made from elastic material.

11. The surgical robot system as defined in claim 9, characterized in that a translation adjustment device is provided on the guide device, said translation adjustment device comprising a further actuating drive and being connected to the surgical instrument in such a way that the shaft of the surgical instrument is movable by the further actuating drive in a z-direction which is orthogonal to the x-direction and y-direction.

12. The surgical robot system as defined in claim 11, characterized in that the translation adjustment device moves the shaft of the surgical instrument in the z-direction by means of a telescopic mechanism and/or a cable winch system.

13. The surgical robot system as defined in claim 9, characterized in that an instrument drive unit is provided on the surgical instrument, said instrument drive unit comprising a rotational actuator, by means of which the shaft of the surgical instrument is variably rotated around the z-direction in relation to the port mechanism.

14. The surgical robot system as defined in claim 13, characterized in that the instrument drive unit preferably comprises three instrument actuators by means of which a work unit of the surgical instrument, arranged on the distal end, is variable in three further degrees of freedom.

15. The surgical robot system as defined in claim 13, characterized in that the instrument drive unit is arranged on the proximal end of a telescopic mechanism by means of a holding device.

16. The surgical robot system as defined in claim 9, characterized in that two guide devices are intended for insertion of two surgical instruments through the compensating element, whereby an adjustment device of a first of the two guide devices is arranged in a mirror-inverted manner with regard to a longitudinal axis of the two guide devices to an adjustment device of a second of the two guide devices.

\* \* \* \* \*